(12) United States Patent
Teramoto et al.

(10) Patent No.: US 8,932,590 B2
(45) Date of Patent: Jan. 13, 2015

(54) METHOD OF ADSORBING TRANSFORMING GROWTH FACTOR β

(75) Inventors: Kazuo Teramoto, Otsu (JP); Toshio Yoshioka, Otsu (JP); Masaaki Shimagaki, Otsu (JP); Takeo Matsunase, Moriyama (JP); Koji Watanabe, Kusatsu (JP); Yuji Ueda, Kyoto (JP); Yoshiki Yamamoto, Kyoto (JP)

(73) Assignee: TORAY Industries, Inc., Tokyo (JP)

( * ) Notice: Subject to any disclaimer, the term of this patent is extended or adjusted under 35 U.S.C. 154(b) by 99 days.

(21) Appl. No.: 13/067,627

(22) Filed: Jun. 15, 2011

(65) Prior Publication Data

US 2011/0240560 A1  Oct. 6, 2011

Related U.S. Application Data

(63) Continuation of application No. 10/516,015, filed as application No. PCT/JP03/04277 on Apr. 3, 2003, now abandoned.

(30) Foreign Application Priority Data

May 30, 2002 (JP) .................. 2002-156867
Aug. 21, 2002 (JP) .................. 2002-240246

(51) Int. Cl.
| | | |
|---|---|---|
| *A61K 39/395* | (2006.01) | |
| *B01J 20/26* | (2006.01) | |
| *B01J 20/28* | (2006.01) | |
| *B01J 20/32* | (2006.01) | |
| *B01J 20/30* | (2006.01) | |
| *A61M 1/36* | (2006.01) | |

(52) U.S. Cl.
CPC ............ *B01J 20/26* (2013.01); *B01J 20/28023* (2013.01); *B01J 20/2803* (2013.01); *B01J 20/28033* (2013.01); *B01J 20/3242* (2013.01); *B01J 20/28014* (2013.01); *B01J 20/261* (2013.01); *B01J 20/262* (2013.01); *B01J 20/265* (2013.01); *B01J 20/321* (2013.01); *B01J 20/3212* (2013.01); *B01J 20/3217* (2013.01); *B01J 20/3251* (2013.01); *B01J 20/3272* (2013.01); *B01J 20/3293* (2013.01); *B01J 20/3092* (2013.01); *B01J 20/28057* (2013.01); *B01J 20/28045* (2013.01); *B01J 20/28016* (2013.01); *A61M 1/3679* (2013.01); *B01J 2220/58* (2013.01); *B01J 2220/60* (2013.01)
USPC .................... 424/138.1; 424/140.1; 424/486; 435/7.23

(58) Field of Classification Search
None
See application file for complete search history.

(56) References Cited

U.S. PATENT DOCUMENTS

| 5,407,581 A | 4/1995 | Onodera et al. .............. 210/654 |
| 2002/0164644 A1 | 11/2002 | Maruyama et al. ............ 435/7.1 |
| 2003/0170234 A1 | 9/2003 | Hellmann .................. 424/142.1 |

FOREIGN PATENT DOCUMENTS

| EP | 1 142 633 A1 | 10/2001 |
| EP | 1 192 963 A1 | 4/2002 |
| WO | 01/74420 A1 | 10/2001 |

OTHER PUBLICATIONS

O. Ishiko et al., "Removal of Immunosuppressive Substance in Cancer Patients' Serum" Japanese J. Cancer Research vol. 81, No. 6-7, pp. 564-566, Jun. 1990.
Supplementary European Search Report issued Aug. 26, 2010, in European Application No. 03756106.5—1270/1532993 (PCT/JP0304277).

*Primary Examiner* — James Rogers
(74) *Attorney, Agent, or Firm* — Kubovcik & Kubovcik

(57) ABSTRACT

An adsorbent for immunosuppressive substance, which can adsorb an excessive immunosuppressive substance directly from a body fluid, can carry out extracorporeal perfusion safely and can be utilized in treatment of cancer. The excessive immunosuppressive substance may be involved in growth of cancer cells. The adsorbent for immunosuppressive substance includes a water-insoluble carrier and a hydrophilic amino group immobilized to the water-insoluble carrier. An extracorporeal perfusion column contains the adsorbent of the invention. A method for treating cancer carries out extracorporeal perfusion using the extracorporeal perfusion column. A method of adsorbing the transforming growth factor β which is combined with another protein, includes adsorbing the transforming growth factor β and protein on an adsorbent containing a water-insoluble carrier to which quaternary ammonium groups each having 3 to 18 carbon atoms per one nitrogen atom are attached, and having a specific surface area of 0.1 m² or more per gram.

6 Claims, No Drawings

METHOD OF ADSORBING TRANSFORMING GROWTH FACTOR β

This application is a continuation of application Ser. No. 10/516,015, filed Aug. 2, 2005 now abandoned, which is a 371 of international application PCT/JP03/04277, filed Apr. 3, 2003, which claims priority based on Japanese Patent Application Nos. 2002-156867 and 2002-240246, filed May 30, 2002, and Aug. 21, 2002, respectively, and which are incorporated herein by reference.

TECHNICAL FIELD

The present invention relates an adsorbent for immunosuppressive substance, an extracorporeal perfusion column and a method for treating cancer.

BACKGROUND ART

Cancer is still one of major causes of death even in today's advanced medicine. Cancer cells cannot be fully removed even by treatment with anticancer agents and/or radiotherapy. Even after tumor was removed by surgery, cancer cells remain in patients with advanced cancer having metastatic foci.

Immunosuppressive substances are possible candidates which prevent the cancer cells from being perfectly removed. Living bodies inherently should have immune functions such as cancer specific killer cells that eliminate cancerous cells. It is conceived that some of immunosuppressive substances are present in the blood of healthy subjects and play a role for controlling immune actions, but some abnormally grow along with the advance of cancer, prevent the induction and expression of the functions of the cancer specific killer cells to thereby suppress the immune functions against the cancer cells and, as a result, assist the growth of the cancer cells.

Known immunosuppressive substances are immunosuppressive proteins such as transforming growth factor beta (subtypes 1 to 5 are known, and they are hereinafter briefly and generically referred to as "TGF β"), immunosuppressive acidic protein, carcinoembryonic antigens, interleukin 6 and tumor necrosis factors (TNFs); prostaglandin E2; and cells such as B cells and macrophages (Hiromi Fujiwara, Tumor Immunology, p. 89-112, Chugai Igaku-sha Ltd., 1998).

Accordingly, removal of immunosuppressive substances holds promise of increasing the immunity of a patient, suppressing the growth of cancer cells and leading the tumor to regression.

Attempts have therefore been made to remove or eliminate immunosuppressive substances such as immunosuppressive acidic protein and carcinoembryonic antigens by plasma exchange (see, for example, Non-patent Document 1). Attempts have also been made to remove immunosuppressive substances by using an apparatus comprising a double membrane plasma separator and an adsorbent made from an amino-group-bearing glass beads for adsorbing immunosuppressive factors having low molecular weights. This technique is intended to reduce a displacement liquid (see, for example, Non-patent Document 2). In addition, combined therapy of plasma exchange and an anticancer agent cyclophosphamide has been attempted (see, for example, Non-patent Document 3). These treatments, however, do not work sufficiently effectively. This is probably mainly because the adsorbents have insufficient adsorptivity. In addition, the plasma exchange has a low removing efficiency and brings a risk of infection of a disease from a plasma donor.

As the TGF β adsorbents, one having a hydrophobic ligand has been disclosed (see Patent Document 1). This technique, however, is intended for an "active TGF β" having a molecular weight of about 25,000 as described in the document, and the document fails to describe a "latent TGF β" having a molecular weight of about $10 \times 10^4$ to $30 \times 10^4$. In general, a compound having an increasing molecular weight among compounds of the same type becomes more difficult to be absorbed by an adsorbent.

Techniques for analyzing the active molecules typically by allowing hydroxyapatite to adsorb and/or desorb TGF β1 in the blood have been disclosed (see Patent Documents 2 to 4). These techniques, however, also intended for the active TGF β.

The immunosuppressive acidic protein is a protein having a molecular weight of about $5 \times 10^4$ and is clinically used as a marker for the malignancy of cancer. An attempt has been made to remove the immunosuppressive acidic protein using an active carbon column (see Non-patent Document 4), but has not yet been used in practice, probably because of its insufficient adsorptivity. The active carbon column is not suitable for applications in which it comes in direct contact of the blood, such as extracorporeal perfusion, since the active carbon often yields powders.

Attempts have been made to treat cancer by subjecting the blood to extracorporeal perfusion using a fiber having a lipopolysaccharide of a gram-negative bacterium immobilized thereto to thereby activate the blood (see Non-patent Document 5 and Patent Documents 5 to 9). The lipopolysaccharide serves as an endotoxin. This fiber, however, is not an adsorbent but a cell activator. In addition, these documents do not refer to the adsorption of immunosuppressive substances.

Patent Documents 10 and 11 each disclose a fiber having an immobilized hydrophilic amine. These techniques, however, are intended for the adsorption of endotoxins, do not refer to the adsorption of immunosuppressive substances and are not intended for the treatment of cancer.

[Non-Patent Document 1]

Toge et al., "Significance of Plasma Exchange Treatment in Cancer Treatment", Biotherapy, vol. 2, 1988, p. 1019-1028

[Non-Patent Document 2]

Kunzo Orita, "Basic and Clinical Researches for Clinical Applications of Double Membrane Plasmapheresis in order to Remove Immunosuppressive Factors in Serum of Patients with Cancer", Gan Chiryo no Ayumi (in Japanese, "Progress in Cancer Treatment"), vol. 4, 1984, p. 18

[Non-Patent Document 3]

Nishioka et al., "Effects of Membrane Plasma Exchange Treatment on Growth Suppression of Tumor of Tumor-bearing Rat—combined effects with immunochemical therapy—", Jinko Zoki (in Japanese, "Artificial Organ"), vol. 14, 1985, p. 361-365

[Non-Patent Document 4]

O. Ishiko et al, Removal of Immunosuppressive Substance in Cancer-Patients' Serum, Jpn J Cancer Res, 81, 564-566, (1990)

[Non-Patent Document 5]

T. Tani et al., Efficacy and Biocompatibility of Nobel anti-Cancer Fiber in Hemoperfusion on Cancer-Bearing Rabbits, Therapeutic Apheresis, 6(2), 167-172, (2000)

[Patent Document 1]

Japanese Unexamined Patent Application Publication No. 2001-218840

[Patent Document 2]
Japanese Unexamined Patent Application Publication No. 7-31875
[Patent Document 3]
Japanese Unexamined Patent Application Publication No. 8-193997
[Patent Document 4]
Japanese Unexamined Patent Application Publication No. 9-80042
[Patent Document 5]
Japanese Unexamined Patent Application Publication No. 59-64053
[Patent Document 6]
Japanese Unexamined Patent Application Publication No. 59-211458
[Patent Document 7]
Japanese Unexamined Patent Application Publication No. 60-2258
[Patent Document 8]
Japanese Unexamined Patent Application Publication No. 60-12071
[Patent Document 9]
Japanese Unexamined Patent Application Publication No. 60-89425
[Patent Document 10]
Japanese Unexamined Patent Application Publication No. 60-197703
[Patent Document 11]
Japanese Unexamined Patent Application Publication No. 60-195455

DISCLOSURE OF INVENTION

Accordingly, an object of the present invention is to provide an adsorbent for immunosuppressive substance in order to contribute to treatment of cancer, which adsorbent can highly efficiently and selectively adsorb an excessive immunosuppressive substance, which may be involved in the growth of cancer cells, directly from a body fluid and can carry out extracorporeal perfusion safely.

Specifically, the present invention provides an adsorbent for immunosuppressive substance, including a water-insoluble carrier and a hydrophilic amino group immobilized to the water-insoluble carrier.

The present invention further provides an extracorporeal perfusion column containing the adsorbent of the present invention.

In addition, the present invention provides a method for treating cancer, including the step of carrying out extracorporeal perfusion with the use of the extracorporeal perfusion column of the present invention.

BEST MODE FOR CARRYING OUT THE INVENTION

The adsorbent for immunosuppressive substance of the present invention comprises a water-insoluble carrier and a hydrophilic amino group immobilized to the water-insoluble carrier. The mechanism that the hydrophilic amino group adsorbs an immunosuppressive substance has not yet been clarified, but the present inventors have verified that the adsorbent adsorbs a variety of immunosuppressive substances, as shown in the examples that will be described later.

The term "hydrophilic" means that an amine that is soluble in water by itself is chemically combined with a polymer. Regarding the number of carbon atoms, the amino group corresponds to an amino group derived from an amine having 18 or less carbon atoms per one nitrogen atom.

Of hydrophilic amino groups, quaternary ammonium groups are preferred, of which quaternary ammonium groups derived from tertiary amines each having 3 to 18 carbon atoms, more preferably 4 to 14 carbon atoms, per one nitrogen atom are specifically preferred for their high adsorptivity. Specific examples of such tertiary amines each having an alkyl group are trimethylamine, triethylamine, N,N-dimethylethylamine, N,N-dimethylpropylamine, N,N-dimethylbutylamine, N,N-dimethylhexylamine, N,N-dimethyloctylamine, N,N-dimethyllaurylamine and N-methyl-N-ethylhexylamine. In addition, amines each having the alkyl group containing a hydroxyl group and/or an ether group are preferably used as hydrophilic amines for constituting the hydrophilic amino group. Examples thereof are N,N-dimethyl-6-hydroxyhexylamine and N,N-dimethyl-4-methoxybutylamine.

The amount of the hydrophilic amino group to be immobilized to the water-insoluble carrier is preferably 0.01 to 2.0 mol, and more preferably 0.1 to 1.0 mol per constitutional repeating unit of the water-insoluble carrier. The adsorptive function can be efficiently manifested by setting the amount at 0.01 mol or more, more preferably 0.1 mol or more. The water-insoluble carrier can maintain its physical strength as a carrier by setting the amount at 2.0 mol or less, more preferably 1.0 mol or less. The amount of the immobilized hydrophilic amino group can be determined according to a method for measuring an ion-exchange capacity of an ion-exchange resin. More specifically, the amount can be determined, for example, in the following manner. One gram of a sample water-insoluble carrier having a immobilized hydrophilic amino group is charged into a column, 50 mL of a 1 mol/L aqueous solution of sodium hydroxide is allowed to pass through the column, and then water is allowed to pass for washing until the eluent does not develop red with phenolphthalein. Then, 10 mL of 1 mol/L hydrochloric acid is allowed to pass through the resulting column, and 300 mL of water is allowed to pass therethrough. The amount of the eluted acid is determined by neutralization titration with a 0.5 mol/L aqueous solution of sodium hydroxide. The amount of the hydrophilic amino group is defined as a value obtained by subtracting the amount of the alkali required for neutralization from 10 mmol. This value is divided by the constitutional repeating unit contained in one gram of the water-insoluble carrier and then can be checked against the above-specified range.

As the water-insoluble carrier, one which is insoluble in water and can bear a hydrophilic amine as an immobilized hydrophilic amino group. Water-insoluble carriers derived from aromatic polymers are preferred, for easier introduction of functional groups. More specific examples of the aromatic polymers are poly(aromatic vinyl compound)s typified by polystyrenes. Alternatively, those derived from polysulfone polymers are preferred for their satisfactory moldability. Typical examples thereof are poly(p-phenylene ether sulfone)s and -{(p-$C_6H_4$)—C($CH_3$)$_2$-(p-$C_6H_4$)—O-(p-$C_6H_4$)—$SO_2$—(p-$C_6H_4$)—O—}$_n$— (hereinafter briefly referred to as "Udel polysulfone"). Those derived from polymers such as poly(ether imide)s, polyimides, polyamides, polyethers and polyphenylenesulfides will also do. A water-insoluble carrier which is soluble in an organic solvent is advantageously employed as the water-insoluble carrier, for its higher moldability.

Examples of a reactive functional group for enabling the polymer to immobilize the hydrophilic amine are active halogen groups such as halomethyl groups, haloacetyl groups, haloacetamidomethyl groups and halogenated alkyl groups, epoxide group, carboxyl group, isocyanate group, thioisocyanate group and acid anhydride groups. Among them, active halogen groups are preferred, of which haloacetyl groups are typically preferred, because they can be easily prepared, have appropriately high reactivity to carry out a reaction for immobilizing the hydrophilic amine under mild conditions and can yield a chemically stable covalent binding formed as a result of the immobilization reaction. Specific examples of the polymer added with such a haloacetyl group are chloroacetamidomethylated polystyrenes, chloroacetamidomethylated Udel polysulfones and chloroacetamidomethylated poly(ether imide)s.

To immobilize the hydrophilic amino group to the water-insoluble carrier, a heterogeneous reaction process and a homogeneous reaction process may be employed. In the heterogeneous reaction process, the water-insoluble carrier which has been molded is brought into contact with a solution of the hydrophilic amine. In the homogeneous reaction process, a solution of the water-insoluble carrier and a solution of the hydrophilic amine are mixed and reacted, and then the mixture is molded.

In the heterogeneous reaction process, a solvent that does not dissolve the water-insoluble carrier but dissolves the hydrophilic amine is preferably used as a solvent for dissolving the hydrophilic amine. Examples of the solvent are water, methanol, ethanol and isopropanol. In the homogeneous reaction process, a solvent that can dissolve both the water-insoluble carrier and the hydrophilic amine is preferably used. Examples thereof are tetrahydrofuran, dimethyl sulfoxide, N,N-dimethylformamide (DMF), N,N-dimethylacetamide and N-methylpyrrolidone.

The heterogeneous reaction process can be carried out, for example, by dipping a molded article of, for example, a hollow fiber of a chloroacetamidomethylated polysulfone in an isopropanol solution of, for example, dimethylhexylamine or polyalkyleneimine and reacting them at temperatures of 0° C. to 100° C. The homogeneous reaction process can be carried out, for example, by adding the hydrophilic amine to a solution of chloroacetamidomethylated polysulfone in an organic solvent and reacting them at temperatures of 0° C. to 100° C. To enable the water-insoluble carrier to be soluble in an organic solvent, the amount of the hydrophilic amine to be added to the solution is preferably 1 fold by mole or more with respect to the reactive functional group serving for immobilization. In the case of a polyamine, the hydrophilic amine is preferably added in large excess.

The adsorbent for immunosuppressive substance of the present invention may be a molded article prepared by molding the water-insoluble carrier having the immobilized hydrophilic amino group into a shape as an adsorbent or may be an article comprising a substrate or base material and the water-insoluble carrier having the immobilized hydrophilic amino group covering the substrate.

The embodiment in which the adsorbent comprises a substrate or base material and the water-insoluble carrier having the immobilized hydrophilic amino group covering the substrate is advantageous in that the resulting adsorbent can easily have a large surface area at low cost. A material for the substrate is preferably one having good adhesion with the water-insoluble carrier having the immobilized hydrophilic amino group. Examples thereof are polyamides, polyurethanes, polyimides, polysulfones, poly(vinyl chloride)s, polyesters, poly(phenylene sulfide)s, polyolefins, polyacrylonitriles and cellulosic resins. Among them, polyamides such as nylons and poly(ether imide)s are typically preferably used, for their high adhesion properties. As the procedure for covering, there are a dry coating process and a wet coating process. In the dry coating process, the water-insoluble carrier having the immobilized hydrophilic amino group or the added hydrophilic amine is dissolved in a low boiling solvent such as methylene chloride or tetrahydrofuran, the substrate such as a knitted fabric or woven fabric of nylon is dipped in the solution, and the solvent is evaporated. In the wet coating process, the water-insoluble carrier having the immobilized hydrophilic amino group or the added hydrophilic amine is dissolved in a solvent such as N,N-dimethylformamide, the substrate is dipped in the solution, and the dipped substrate is further placed in a poor solvent such as water.

The specific surface area of the adsorbent for immunosuppressive substance of the present invention is preferably 0.1 $m^2$ or more, and more preferably 1 $m^2$ or more per one gram of the adsorbent, for improving the adsorptivity and adsorption capacity. The specific surface area, however, cannot be increased without limitation and is, in practice, preferably 100 $m^2$ or less. The surface area can be determined by a nitrogen gas adsorption process (BET process).

The adsorbent for immunosuppressive substance of the present invention preferably has a shape selected from a film shape, a fibrous shape, a spongiform shape, a granular shape and a combination of these shapes. By configuring thus, the adsorbent can have a large specific surface area and exhibit sufficient permeability with respect to, for example, the body fluid. Such fibers can be formed into, for example, a filament, a flocculent substance, a knitted fabric, a woven fabric or a felt. Among such fibers, hollow fibers are also preferred. By configuring the adsorbent into hollow fibers, the resulting adsorbent also has the function of filtration, and the extracorporeal circulation column can serve to remove the immunosuppressive substance while serving also as a dialyzing unit or a plasma separator.

The immunosuppressive substance to be adsorbed by the adsorbent for immunosuppressive substance of the present invention preferably comprises an immunosuppressive protein.

More preferably, the immunosuppressive protein comprises at least one selected from a transforming growth factor beta, immunosuppressive acidic protein and a carcinoembryonic antigen.

The TGF β is preferably a latent TGF β. TGF β by itself is a protein having a molecular weight of about 25000, but is combined with another protein to constitute a protein having a molecular weight of about $10 \times 10^4$ (low-molecular-weight latent TGF β) or a protein having a molecular weight of about $30 \times 10^4$ (high-molecular-weight latent TGF β) in the blood, and these must be removed or eliminated from the blood of a patient with cancer efficiently.

The immunosuppressive substance to be adsorbed preferably comprises prostaglandin-E2.

It may also be preferred that the adsorbent is capable of adsorbing plural different immunosuppressive substances, from the view point of effective treatment of cancer.

The adsorbent for immunosuppressive substance of the present invention is preferably used in an extracorporeal perfusion column, as mentioned below. It can also be used for the purpose of removing one or more immunosuppressive proteins from the blood supply, serum or plasma.

Next, the extracorporeal perfusion column of the present invention comprises the adsorbent for immunosuppressive substance of the present invention. The resulting extracorporeal perfusion column is suitable for cancer treatment by extracorporeal perfusion or by combined therapy with extracorporeal perfusion.

The extracorporeal perfusion column of the present invention can have, for example, a cylindrical, rectangular, discoidal or doughnut-like shape.

The adsorbent is preferably charged so that the volume of voids is about 200 mL or less for reducing the burdens on the patient.

The amount of the adsorbent for immunosuppressive substance of the present invention contained in the extracorporeal perfusion column of the present invention is preferably set so that the adsorptivity of the column is 250 ng or more per 1 kg of the body weight of a tumor-bearing mammal to be treated. The adsorptivity herein is in terms of TGF β including a latent type and an active type as a primary standard. In this connection, most of TGF β is present as the latent type in the blood. The absorptivity herein is obtained by multiplying an equilibrium adsorption for a latent TGF β per one gram of the adsorbent by grams of the charged adsorbent in the column.

The equilibrium adsorption for a latent TGF β can be determined in the following manner. Specifically, 50 mg of the adsorbent is placed in 1 mL of the serum of a tumor-bearing rat, the mixture is shaken at 37° C. for four hours, the TGF β level in the supernatant is determined, and the difference in the TGF β levels between before and after absorption is divided by the weight of the adsorbent (0.05 g) to give the equilibrium adsorption for a latent TGF β. The TGF β level in the supernatant can be determined by pretreating the sample serum with an acid to allow the latent TGF β to be converted into a free active TGF β, and determining the level by an enzyme immunoassay using an anti-TGF β antibody and a commercially available assay kit.

The "tumor-bearing mammal" means a terrestrial mammal bearing tumor derived from cancer. Examples of the terrestrial mammal are humans, monkeys, cows, horses, dogs, cats, pigs and sheep.

The method for treating cancer of the present invention comprises the step of carrying out extracorporeal circulation with the use of the extracorporeal perfusion column of the present invention. This method can adsorb and eliminate an immunosuppressive substance from the blood in extracorporeal perfusion, suppress the growth of cancer cells and effectively treat the cancer. The "treatment (or treating)" herein means and includes not only complete recovery but also suppression of the advance of cancer, prevention of metastasis and improvement in quality of life of the patient in broad meanings.

More specifically, the extracorporeal circulation can be carried out, for example, in the following manner. A puncture catheter for collection of blood, a drip chamber connected to an infusion pump for continuously administering an anticoagulant such as heparin or futhan, a blood pump, a drip chamber, the extracorporeal perfusion column of the present invention, a drip chamber, and a puncture catheter for reinfusion are combined in this order using tubes each having an appropriate diameter to form an extracorporeal perfusion system, and the blood is allowed to pass through the system. The blood collection and reinfusion may be carried out by pricking to the artery or vein of the femur or arm. For a big mammal, a commercially available extracorporeal perfusion apparatus and a blood cycle for a hemodialyzer or an adsorptive blood purifier can be used. The extracorporeal perfusion is preferably carried out for 10 minutes to 300 minutes, and generally for 30 minutes to 120 minutes.

As is described above, the method for treating cancer of the present invention is preferably used for treating a tumor-bearing mammal, in which the absorptivity of the extracorporeal perfusion column is 250 ng or more per 1 kg of the body weight of the tumor-bearing mammal.

According to the method for treating cancer of the present invention, the extracorporeal perfusion is preferably carried out in combination with the administration of an antineoplastic agent. Thus, the cancer can be treated while reducing adverse drug reactions of the antineoplastic agent.

Examples of the antineoplastic agent are antimetabolic antineoplastic agents such as gemcitabine, fluorouracil, tegafur, cytarabine and methotrexate; alkylating agents typified by cyclophosphamide; alkaloid antineoplastic agents such as vincristine, vinblastine, vindesine, etoposide, irinotecan, docetaxel and paclitaxel; antibiotic antineoplastic agents such as doxorubicin, epirubicin, pirarubicin, daunorubicin, mitomycin C, actinomycin D, peplomycin, neocarzinostatin and bleomycin; enzyme inhibitory antineoplastic agents such as gefitinib; as well as cisplatin and carboplatin.

Among them, the antimetabolic antineoplastic agents are preferred, since they have relatively low risks of adverse drug reactions and toxicity.

Of the antimetabolic antineoplastic agents, gemcitabine is slowly metabolized in tumor cells, keeps its antitumor effects over a long time, exhibits antitumor effects against many solid tumors and is typically preferred.

The antineoplastic agent can be administered, for example, by a process of injecting into a tissue near to the tumor, a process of intravenous injection, a process of intramuscular injection or a process of administering orally. The administration process is preferably appropriately selected according to the properties of the drug. The dose is preferably set at one-hundredths or more and one half or less the appropriate dose designated on the antineoplastic agent, because the effects of the drug are enhanced by the combination use of the column for removing an immunosuppressive substance. Regarding the administration time, the antineoplastic agent is administered, for example, preferably 24 to 200 hours, and more preferably 24 to 100 hours before the extracorporeal perfusion.

According to the method for treating cancer of the present invention, the extracorporeal perfusion is also preferably carried out in combination with the excision of a primary focus of the cancer. Cancer cells liberated upon surgical excision may come into the blood vessels and/or lymphatics to cause metastasis. The method of the present invention, however, can also suppress the growth of such metastasized cancer cells and can thereby effectively treat the cancer, which results in the suppression of the metastasis of cancer.

The present invention will be illustrated in further detail with reference to several examples below, which are not intended to limit the scope of the invention.

[Preparation of Test Animal]

(1) Tumor-Bearing Rat 1

YS cells ($2\times10^8$) (available from Institute of Development, Aging and Cancer, Tohoku University) were hypodermically inoculated to the back of male HOS:Donryu rats of an age of 8 weeks to yield Tumor-bearing Rats 1.

(2) Tumor-Bearing Rat 2

To the back of male WKAH:Hkm rats of an age of 12 weeks were hypodermically inoculated $2\times10^6$ of 4-dimethylaminoazobenzene-induced hepatic carcinoma cells KDH-8 [Satoshi Yano, "Hokkaido Igaku Zasshi" (in Japanese, Medical Journal of Hokkaido), 68, 5, 654-664 (1993)]. The cancer cells generally begin to grow one week after inoculation and cause death of the subject 5.5 weeks after inoculation.

[Measuring Method]

(1) Specific Surface Area of Adsorbent

After evacuation at 100° C., an adsorption isotherm was determined at 77 K in an atmosphere of nitrogen gas using a high-precision full automatic gas adsorber "BELSORP 36" available from Bel Japan, Inc. The specific surface area was determined by applying the BET multimolecular adsorption theory to the isotherm.

(2) TGF β Equilibrium Adsorptivity of Adsorbent

The sera of five Tumor-bearing Rats 1 were collected to yield 30 mL of a tumor-bearing rat serum. A total of 50 mg of a sample adsorbent was placed into 1 mL of the prepared serum, followed by shaking at 37° C. for 4 hours. The TGF β level in the supernatant was determined according to the following method (3) for "TGF β Level". The TGF β equilibrium adsorptivity was obtained by dividing the difference in levels between before and after the adsorption by the weight of the adsorbent (0.05 g).

(3) TGF β Level

The TGF β level was determined by using a human TGF-β1 immunoassay kit available from Genzyme TECHNE according to the description in the manual.

(4) Immunosuppressive Acidic Protein Level

The level of immunosuppressive acidic protein was determined by using a Rat IAP Plate available from Sanko Junyaku Co., Ltd.

(5) Albumin Level

The albumin level was determined by using an albumin assay kit "Albumin B-Test Wako".

(6) Adsorption Rate for PGE2

The PGE2 level was determined by using a PGE2 Assay Kit available from NEOGEN Corporation. The adsorption rate was determined by calculation by dividing the serum PGE2 level after adsorption by the serum PGE2 level before adsorption.

(7) Tumor Volume

The dimensions of the tumor region of a rat were measured using micrometer calipers. The longest diameter of the tumor was defined as the major axis, and a diameter of the tumor passing through the midpoint of the major axis in a direction perpendicular to the major axis was defined as the minor axis. The tumor volume was defined according to the following equation:

Tumor Volume=(Major Axis)×(Minor Axis)×(Minor Axis)×0.5[Adsorbent for TGF β and Immunosuppressive Acidic Protein]

(Water-Insoluble Carrier)

An island-in-sea conjugated fiber with 36 islands was prepared by using the following components under yarn-making conditions of a spinning speed of 800 m/min. and a draw ratio of 3 folds. The islands herein each have a sheath-core conjugated structure.

Core component of island: polypropylene

Sheath component of island: 90% of polystyrene, and 10% of polypropylene

Sea component: poly(ethylene terephthalate) copolymerized with 3% of 5-sodiosulfoisophthalic acid Conjugate ratio; core:sheath:sea=40:40:20

The sea component was dissolved in a hot aqueous solution of sodium hydroxide, to thereby yield Original Yarn 1 having a diameter of 4 μm as a sheath-core polypropylene-reinforced polystyrene fiber.

The above procedure was repeated to yield Original Yarn 2 having a diameter of 10 μm and Original Yarn 3 having a diameter of 50 μm, except for appropriately changing the discharge amount and/or draw ratio at the constant conjugate ratio of the sheath and core.

(Intermediate)

A total of 3 g of paraformaldehyde was dissolved in a mixture of 600 mL of nitrobenzene and 390 mL of sulfuric acid at 20° C. The solution was cooled to 0° C., and 75.9 g of N-methylol-α-chloroacetamide was added to and dissolved in the solution at 5° C. or below. A total of 10 g of Original Yarn 1 was dipped therein and was left stand at room temperature for two hours. The fiber was taken out and was placed in large excess of cooled methanol for washing. After fully washing with methanol, the fiber was washed with water and was dried to yield 15.0 g of α-chloroacetamidomethylated polystyrene fiber (Intermediate 1). Intermediate 1 was also used as Comparative Example 1. Likewise, Intermediate 2 (yield: 14.4 g) and Intermediate 3 (yield: 12.5 g) were prepared from 10 g of Original Yarn 2 and 10 g of Original Yarn 3, respectively.

(Immobilization of Hydrophilic Amine by Heterogeneous Reaction)

N,N-dimethylhexylamine (50 g) and potassium iodide (8 g) were dissolved in 360 mL of DMF, and 5 g of Intermediate 1 was dipped in the resulting solution, followed by heating in a bath at 85° C. for three hours. The fiber was then immersed in a 1 mol/L aqueous sodium chloride solution, was then washed with water, was dried in vacuo and thereby yielded 7.3 g of dimethylhexylammonium-modified fiber (Example 1).

Separately, N,N-dimethyloctylamine (50 g) and potassium iodide (8 g) were dissolved in 360 mL of DMF, and 5 g of Intermediate 1 was dipped in the resulting solution, followed by heating in a bath at 85° C. for three hours. The fiber was washed with isopropanol, was immersed in a 1 mol/L aqueous sodium chloride solution, was washed with water, was dried in vacuo and thereby yielded 8.3 g of dimethyloctylammonium-modified fiber (Example 2).

Further separately, N,N-dimethyllaurylamine (50 g) and potassium iodide (8 g) were dissolved in 360 mL of DMF, and 5 g of Intermediate 1 was dipped in the resulting solution, followed by heating in a bath at 85° C. for three hours. The fiber was washed with isopropanol, was immersed in a 1 mol/L aqueous sodium chloride solution, was washed with water, was dried in vacuo and thereby yielded 9.3 g of dimethyllaurylammonium-modified fiber (Example 3). Intermediate 2 and Intermediate 3 were treated by the same procedure and thereby yielded Example 4 having a specific surface area of 1.4 m²/g and Referential Example 1 having a specific surface area of 0.04 m²/g, respectively.

(Immobilization of Nonhydrophilic Amine by Heterogeneous Reaction)

A total of 50 g of stearylamine as a nonhydrophilic amine was dissolved in 360 mL of ethanol, and 5 g of Intermediate 1 was dipped in the resulting solution, followed by heating in a bath at 85° C. for three hours. The fiber was washed with isopropanol, was washed with water, was dried in vacuo and thereby yielded 7.2 g of stearylaminated fiber (Comparative Example 2).

(Sulfonated Fiber)

A total of 5 g of Original Yarn 1 was dipped in a solution of 500 mg of paraformaldehyde in 50 mL of sulfuric acid, followed by heating at 95° C. for one hour. By sequentially carrying out washing with water, washing with a 1 mol/L aqueous sodium chloride solution, washing with water and drying, 7.3 g of a sulfonated fiber (Comparative Example 3) was prepared.

(Synthesis and Coating of Hydrophilic Amine-Bonded Polymer)

A mixture of 16 mL of nitrobenzene and 32 mL of sulfuric acid was cooled to 0° C., and the whole quantity of 4.2 g of N-methylol-α-chloroacetamide was dissolved therein. The whole quantity of the resulting solution was added to a solution of a Udel polysulfone (P3500, available from Teijin Amoco Engineering Plastics Ltd.) in nitrobenzene (300 g/3 L) at 10° C. with sufficient stirring. The mixture was further stirred at room temperature for three hours. The reaction mixture was placed into large excess of cooled methanol to precipitate a polymer. The precipitate was fully washed with methanol, was dried, was resolidified from a mixture of dimethylformamide and methanol and thereby yielded 303 g of α-chloroacetamidomethylated polysulfone having a rate of substitution of 0.05 (Polymer A).

The whole quantities of a solution of 60 g of polyethyleneimine having an average molecular weight of 10000 (Wako Pure Chemical Industries, Ltd.) in 300 mL of DMF and a solution of 30 g of Polymer A in 300 mL of DMF were mixed, followed by stirring at room temperature for 48 hours. The reaction mixture was added to large excess of brine, and the precipitated polymer was separated by filtration. After washing with water, the polymer was dried, was resolidified from a mixture of dimethylformamide and methanol and thereby yielded 27 g of N-alkylated polyalkyleneimine-immobilized polysulfone (Polymer B).

A total of 20 g of a flocculent substance of a poly(ethylene terephthalate) fiber having a diameter of monofilament of 3.5 µm was dipped in a solution of 5 g of Polymer B in 250 mL of methylene chloride. The flocculent substance was taken out 20 hours later, from which the fluid was removed, was air-dried and thereby yielded 21 g of a coated flocculent substance (Example 5). A flocculent substance of the poly(ethylene terephthalate) fiber which had not been coated was used as Comparative Example 5.

(Adsorbent Having Nonionic Functional Group)

A total of 20 g of a flocculent substance of a poly(ethylene terephthalate) fiber having a diameter of monofilament of 3.5 µm was dipped in a solution of 5 g of cellulose acetate in 250 mL of methylene chloride. The flocculent substance was taken out 20 hours later, from which the fluid was removed, was air-dried and thereby yielded 21 g of a coated flocculent substance (Comparative Example 4).

(Determination of Adsorptivity)

Two or three hours after the inoculation of cancer cells, the blood was collected from five Tumor-bearing Rats 1 and thereby yielded 30 mL of a tumor-bearing rat serum. Each of the adsorbents (50 mg) was placed into 1 mL of the serum, followed by shaking at 37° C. for four hours. The protein levels in the supernatants were determined, and the results are shown in Table 1.

TABLE 1

| | Specific surface area ($m^2$/g) | Carbon number per one nitrogen atom of hydrophilic amine | Level of each component (mg/dL) | | |
|---|---|---|---|---|---|
| | | | TGF β1 (ng/mL) | Immunosuppressive acidic protein (µg/mL) | Albumin (g/dL) |
| Non-treated serum | — | — | 92 | 880 | 2.8 |
| Ex. 1 | 2.3 | 8 | 21 | 510 | 2.4 |
| Ex. 2 | 1.9 | 10 | 54 | 670 | 2.5 |
| Ex. 3 | 1.6 | 14 | 73 | 820 | 2.6 |
| Ex. 4 | 1.4 | 14 | 75 | 800 | 2.6 |
| Ex. 5 | 1.1 | 2 | 74 | 748 | 2.6 |
| Com. Ex. 1 | 2.0 | — | 92 | 882 | 2.7 |
| Com. Ex. 2 | 2.0 | 20 | 92 | 872 | 2.6 |
| Com. Ex. 3 | 2.0 | — | 92 | 867 | 2.6 |
| Ref. Ex. 1 | 0.04 | 14 | 90 | 870 | 2.6 |
| Com. Ex. 4 | 1.1 | — | 92 | 846 | 2.7 |
| Com. Ex. 5 | 1.1 | — | 92 | 850 | 2.6 |

[Adsorbent for Prostaglandin E2]

Fibers were prepared by the procedures of Example 1 and Comparative Example 1, respectively.

The fiber corresponding to Intermediate 1 (Comparative Example 1) had a yield of 15.2 g. The fiber corresponding to Example 1 had a yield of 7.4 g and a specific surface area of 2.4 $m^2/g$.

A coated flocculent substance was prepared by the procedure of Example 5.

Polymer A and Polymer B had yields of 305 g and 28 g, respectively. The coated flocculent substance corresponding to Example 5 had a yield of 21 g and a specific surface area of 1.2 $m^2/g$.

(Determination of Adsorptivity)

The blood was collected from above-mentioned Tumor-bearing Rats 1 and thereby yielded 6 mL of a serum having PGE2 level of 1700 ng/mL. A total of 50 mg of a sample fiber was placed in 1 mL of the serum, followed by shaking at 37° C. for two hours.

Before extracorporeal perfusion, these extracorporeal perfusion columns were preliminarily washed with 10 mL of physiological saline containing 1000 units of a heparin sodium injection available from Takeda Pharmaceutical Co., Ltd. and was further washed with 500 mL of physiological saline.

(Extracorporeal Perfusion Treatment)

Two weeks after the inoculation of KDH cells, the rats were subjected to extracorporeal perfusion at a blood flow rate of 2 mL/min. for 30 minutes. The blood was collected from the femoral artery, was allowed to pass through the adsorbent column and was returned to the femoral vein. A heparin sodium injection available from Takeda Pharmaceutical Co., Ltd. was continuously injected at a rate of 100 U/h during the extracorporeal perfusion.

The blood of the rats before and after the extracorporeal perfusion was collected. The TGF β levels in sera were determined and the survival time after inoculation of the cancer cells was observed. The results are shown in Table 2.

TABLE 2

| | Column | | Body weight of rat (kg) | Amount of Adsorbent per 1 kg of rat body weight (g) | TGF β adsorptivity per 1 kg of rat body weight (ng) | Blood TGF β level | | Survival time of rat after inoculation of cancer cells (week) |
|---|---|---|---|---|---|---|---|---|
| | Amount of adsorbent (g) | TGF β adsorptivity (ng) | | | | Before treatment (ng/mL) | After treatment (ng/mL) | |
| Ex. 6 | 0.46 | 230 | 0.32 | 1.4 | 719 | 30.0 | 4.8 | 9.0 |
| Ex. 7 | 0.40 | 200 | 0.31 | 1.3 | 645 | 33.6 | 10.0 | 8.3 |
| Ex. 8 | 0.38 | 190 | 0.34 | 1.1 | 559 | 35.1 | 21.3 | 7.0 |
| Ex. 9 | 0.21 | 107 | 0.38 | 0.55 | 282 | 68.4 | 38.3 | 5.9 |
| Ref. Ex. 2 | 0.16 | 80 | 0.37 | 0.43 | 216 | 67.3 | 58.9 | 4.0 |
| Com. Ex. 6 | 0.43 | 0 | 0.31 | 1.4 | 0 | 34.2 | 34.2 | 4.3 |
| Com. Ex. 7 | 0.43 | 0 | 0.31 | 1.4 | 0 | 35.8 | 35.7 | 4.3 |
| Com. Ex. 8 | 0.43 | 0 | 0.38 | 1.1 | 0 | 67.9 | 67.8 | 3.0 |

The fiber corresponding to Example 1 had a PGE2 adsorption rate of 80%.

The coated flocculent substance corresponding to Example 5 had a PGE2 adsorption rate of 62%.

The fiber corresponding to Comparative Example 1 had a PGE2 adsorption rate of 33%.

[Extracorporeal Perfusion Treatment]

(Preparation of Extracorporeal Perfusion Column)

Extracorporeal perfusion columns were prepared by charging 0.46 g (Example 6), 0.40 g (Example 7), 0.38 g (Example 8), 0.21 g (Example 9) and 0.16 g (Referential Example 2) of a nonwoven fabric respectively into five cylindrical polypropylene columns having an inner diameter of 1 cm and an inner capacity of 2 ml. The nonwoven fabric was prepared from a fiber which had been prepared by the procedure of Example 1 and had a TGF β equilibrium adsorptivity of 500 ng/g.

An extracorporeal perfusion column (Comparative Example 6) was prepared by charging 0.43 g of a nonwoven fabric into the cylindrical column. The nonwoven fabric was made from a fiber prepared by the procedure of Comparative Example 3 and had a TGF β equilibrium adsorptivity of 0 ng/g.

Extracorporeal perfusion columns (Comparative Examples 7 and 8) were prepared by charging 0.43 g each of a nonwoven fabric of a poly(ethylene terephthalate) fiber having a diameter of monofilament of 3.5 μm respectively into two pieces of the cylindrical columns.

[Combined Treatment of Anticancer Agent and Extracorporeal Perfusion]

(Extracorporeal Perfusion Column)

An extracorporeal perfusion column for treating cancer was prepared by charging 0.40 g of a nonwoven fabric made from a fiber corresponding to Example 1 into a cylindrical polypropylene column having an inner diameter of 1 cm and an inner capacity of 2 mL.

(Administration of Anticancer Agent)

One week after the inoculation of cancer cells (rat body weight: 400 to 430 g), 0.6 mg of gemcitabine hydrochloride was injected in the vicinity of the tumor. The gemcitabine hydrochloride used herein was prepared by dissolving an injection preparation thereof (available from Eli Lilly Japan K.K.) in physiological saline to yield a 20 mg/mL solution.

(Extracorporeal Perfusion Treatment)

Before extracorporeal perfusion, the extracorporeal perfusion column for treating cancer was preliminarily washed with physiological saline containing 1000 units of a heparin sodium and was further washed with 500 mL of physiological saline.

Two days after the administration of the anticancer agent, the rats were subjected to extracorporeal perfusion. In an extracorporeal perfusion system, the blood was collected from the femoral artery, was allowed to pass through the extracorporeal perfusion column for treating cancer and was returned to the femoral vein. The extracorporeal perfusion was carried out at a blood flow rate of 2 mL/min. for one hour.

A heparin sodium injection available from Takeda Pharmaceutical Co., Ltd. was continuously injected at a rate of 200 U/h during the extracorporeal perfusion.

Six rats were treated, and the tumor volumes after the inoculation of cancer cells were determined. The results are shown in Table 3 as Examples 10 to 15. The results of six non-treated rats (Comparative Examples 9 to 14) are shown in Table 4. The results in Comparative Examples 15 to 20, in which the anticancer agent was administered but the extracorporeal perfusion treatment was not carried out, are shown in Table 5.

TABLE 3

| | Tumor volume (mL) Time after inoculation of cancer cells | | | |
| --- | --- | --- | --- | --- |
| | 14 days | 21 days | 28 days | 35 days |
| Example 10 | <0.06 | 0.17 | 0.17 | <0.06 |
| Example 11 | <0.06 | 0.17 | 0.17 | <0.06 |
| Example 12 | <0.06 | 0.26 | 1.69 | 2.5 |
| Example 13 | <0.06 | 0.17 | 0.50 | 1.0 |
| Example 14 | <0.06 | 0.26 | 0.86 | 1.5 |
| Example 15 | <0.06 | 0.26 | 1.37 | 2.5 |
| Average tumor volume | <0.06 | 0.22 | 0.79 | 1.3 |

TABLE 4

| | Tumor volume (mL) Time after inoculation of cancer cells | | | |
| --- | --- | --- | --- | --- |
| | 14 days | 21 days | 28 days | 35 days |
| Comparative Example 9 | 1.2 | 6.3 | 22.3 | 56 |
| Comparative Example 10 | 0.90 | 5.0 | 20.2 | 88 |
| Comparative Example 11 | 2.7 | 14.0 | 53 | 94 |
| Comparative Example 12 | 1.5 | 9.2 | 35 | 71 |
| Comparative Example 13 | 2.2 | 12.1 | 37 | 66 |
| Comparative Example 14 | 0.45 | 2.6 | 12.5 | 51 |
| Average tumor volume | 1.5 | 8.2 | 30 | 71 |

TABLE 5

| | Tumor volume (mL) Time after inoculation of cancer cells | | | |
| --- | --- | --- | --- | --- |
| | 14 days | 21 days | 28 days | 35 days |
| Comparative Example 15 | <0.06 | 4.3 | 26 | 41 |
| Comparative Example 16 | <0.06 | 7.9 | 41 | 59 |
| Comparative Example 17 | <0.06 | 6.6 | 24 | 38 |
| Comparative Example 18 | <0.06 | 7.4 | 35 | 54 |
| Comparative Example 19 | <0.06 | 7.0 | 30 | 47 |
| Comparative Example 20 | <0.06 | 4.5 | 25 | 37 |
| Average tumor volume | <0.06 | 6.3 | 30 | 46 |

In Examples 10 to 15 shown in Table 3, DHP (direct hemoperfusion) treatment was carried out Day 2 of the administration of gemcitabine hydrochloride. In Examples 10 and 11, the tumor completely disappeared. The tumor growth speeds in Examples 12 to 15 were significantly reduced as compared with Comparative Examples 11 to 16 (Table 4) which had not been treated. In the comparative examples shown in Table 5, gemcitabine hydrochloride was administered but the extracorporeal perfusion treatment was not carried out. They show suppression effects in the first week (Day 14) but exhibit no difference from the non-treated group, upon comparison between Table 4 and Table 5. In contrast, the growth of tumor was significantly suppressed and one third of the subjects (rats) were completely cured in the examples.

(Visual Observation of Tumor Metastasis)

The test procedures of Examples 10 to 15 and Comparative Examples 11 to 22 were repeated, except for using three other rats (Examples 16 to 18, and Comparative Examples 21 to 26). The metastasis of the tumor to a region other than beneath the back skin to which the tumor was inoculated was visually observed (Table 6). The rats were dissected 35 days after the extracorporeal perfusion, and the tumor was observed. As a result, the metastasis was hardly observed in cases in which the extracorporeal perfusion treatment was carried out two days into the administration of gemcitabine hydrochloride.

TABLE 6

| | Metastasis (visual observation) | Note (treatment method) |
| --- | --- | --- |
| Example 16 | none | anticancer agent and extracorporeal perfusion |
| Example 17 | none | anticancer agent and extracorporeal perfusion |
| Example 18 | dermic micrometastasis (2 mm diameter) near to the right axillary of antebrachium | anticancer agent and extracorporeal perfusion |
| Com. Ex. 21 | dermic metastasis near to the breast bone | not treated |
| Com. Ex. 22 | dermic metastasis near to the right axillary of antebrachium, and pulmonary metastasis | not treated |
| Com. Ex. 23 | dermic metastases near to the right axillary of antebrachium and near to the breast bone | not treated |
| Com. Ex. 24 | dermic metastasis near to the breast bone | administration of anticancer agent alone |
| Com. Ex. 25 | dermic micrometastasis (2 mm diameter) near to the right axillary of antebrachium | administration of anticancer agent alone |
| Com. Ex. 26 | dermic micrometastasis (2 mm diameter) near to the right axillary of antebrachium | administration of anticancer agent alone |

INDUSTRIAL APPLICABILITY

The present invention can provide the adsorbent for immunosuppressive substance, which can selectively and highly efficiently adsorb an excessive immunosuppressive substance directly from the body fluid. Such an immunosuppressive substance is supposed to be involved in the growth of cancer cells. The adsorbent for immunosuppressive substance can be safely used in extracorporeal perfusion and can be utilized in treatment of cancer.

The invention claimed is:

1. A method of treating cancer of a tumor-bearing mammal by adsorbing transforming growth factor β having a molecular weight of about 25,000 which is combined with another protein, said method comprising providing an extracorporeal perfusion column containing an adsorbent comprising a water-insoluble carrier having a surface to which quaternary ammonium groups are attached, each quaternary ammonium group having 8 to 18 carbon atoms per one nitrogen atom and at least one carbon chain having not less than 6 carbon atoms, said adsorbent having a specific surface area of 0.1 m² or more per one gram, said extracorporeal perfusion column containing said adsorbent in an amount such that the adsorptivity of the transforming growth factor β of the extracorporeal perfusion column is 250 ng or more per 1 kg of the body weight of said tumor-bearing mammal; and conducting extracorporeal perfusion of a body fluid of the tumor-bearing mammal through said extracorporeal perfusion column.

2. The method according to claim 1, wherein said water insoluble carrier is derived from a polysulfone polymer.

3. The method according to claim 1, wherein said water insoluble carrier is derived from a poly(aromatic vinyl compound).

4. The method according to claim 1, wherein said adsorbent is a molded article prepared by molding a water insoluble polymer to which said quaternary ammonium groups are attached into a shape selected from the group consisting of a film shape, a fibrous shape, a spongiform shape, a granular shape and a combination of these shapes.

5. The method according to claim 1, wherein said adsorbent comprises a substrate or base material covered with a water insoluble polymer to which said quaternary ammonium groups are attached, said substrate or base material having a shape selected from the group consisting of a film shape, a fibrous shape, a spongiform shape, a granular shape and a combination of these shapes.

6. The method according to claim 1, wherein said adsorbent has a capacity of adsorbing said transforming growth factor β having a molecular weight of about 25,000 combined with another protein, in an amount of 340 ng or more per one gram of said adsorbent.

* * * * *